United States Patent [19]
Durif et al.

[11] Patent Number: 5,939,094
[45] Date of Patent: Aug. 17, 1999

[54] TRANSDERMAL ADMINISTRATION OF APOMORPHINE

[75] Inventors: Franck Durif, Durtol, France; Ragab El-Rashidy, Deerfield, Ill.

[73] Assignee: Pentech Pharamaceticals, Inc., Buffalo Grove, Ill.

[21] Appl. No.: 08/727,189

[22] Filed: Oct. 8, 1996

Related U.S. Application Data

[63] Continuation-in-part of application No. 08/362,831, Dec. 23, 1994, Pat. No. 5,562,917.

[51] Int. Cl.$^6$ ........................................... A61F 13/02
[52] U.S. Cl. ............................................ 424/448; 424/449
[58] Field of Search ..................................... 424/448, 449

[56] References Cited

U.S. PATENT DOCUMENTS

| | | |
|---|---|---|
| 2,490,357 | 12/1949 | Hyde . |
| 2,542,334 | 2/1951 | Hyde . |
| 2,676,182 | 4/1954 | Daudt et al. . |
| 2,927,907 | 5/1960 | Polmanteer . |
| 3,002,951 | 10/1961 | Johannson . |
| 3,161,614 | 12/1964 | Brown et al. . |
| 3,186,967 | 6/1965 | Nitzsche et al. . |
| 3,459,731 | 8/1969 | Gramera et al. . |
| 3,509,191 | 4/1970 | Atwell . |
| 3,697,473 | 10/1972 | Polmanteer et al. . |
| 4,584,355 | 4/1986 | Blizzard et al. . |
| 4,585,936 | 4/1986 | Homan et al. . |
| 4,591,622 | 5/1986 | Blizzard et al. . |
| 4,655,767 | 4/1987 | Woodward et al. . |
| 4,837,027 | 6/1989 | Lee ........................................... 424/449 |
| 4,978,532 | 12/1990 | El-Rashidy ............................... 424/448 |

OTHER PUBLICATIONS

Arkles, B., *Chemtech* 13: 542–555 (1983).
Colosimo, C., et al., *Clinical Neuropharmacology*, 17: 243–259 (1994).
Deffond, D., et al., *J. Neurol. Neurosurg. Psychiatry* 56: 101–103 (1993).
Durif, F., et al., *Clinical Neuropharmacology* 17:445–453 (1994).
Durif, F., et al., *Eur. J. Clin. Pharmacol.* 41: 493–494 (1991).
Gancher, S.T., et al. *Movement Disorders* 6:212–216 (1991).
Hughes, A.J., et al., *Movement Disorders* 6: 165–170 (1993).
Montastuc, J.L., et al. *Clinical Neuropharmacology* 14:432–437 (1991).
Müller et al., *J. Pharmaceut. Sci.* 75 571–572 (1986).
Pfister, W. R., *Pharmaceutical Technol.* 13: 126–138 (1989).
Tanaka, T. *Sci. Amer.* 244: 124–138 (1981).

*Primary Examiner*—D. Gabrielle Brouillette
*Attorney, Agent, or Firm*—Olson & Hierl, Ltd.

[57] ABSTRACT

Dosage forms for the transdermal administration of apomorphine are described. The dosage forms are water-soluble gel compositions that contain apomorphine, optionally together with a permeation enhancer, or transdermal patches.

13 Claims, 5 Drawing Sheets

TRANSDERMAL ADMINISTRATION OF APOMORPHINE

REFERENCE TO RELATED APPLICATION

This is a Continuation-In-Part Application of U.S. Ser. No. 08/362,831, filed Dec. 23, 1994, which issued as U.S. Pat. No. 5,562,917.

TECHNICAL FIELD

The present invention is directed to drug delivery dosage forms for transdermal administration of apomorphine to a patient. The dosage forms are gel compositions that contain apomorphine, optionally together with a permeation enhancer, in a water-soluble gel.

BACKGROUND OF THE INVENTION

Parkinson's disease is a progressive degenerative disorder of the central nervous system characterized by a loss of neurons in a particular region of the brain, the substantia nigra. These neurons, when present, synthesize and release dopamine, the neurotransmitter used in chemical communication with other cells, and are thus referred to as dopaminergic neurons. Symptoms of Parkinson's disease, including rigidity, resting tremor (shaking), poverty of movement (akinesia), slowness of movement (bradykinesia), and changes in gait and posture, can be severely debilitating, causing a profound change in the quality of life for the spouse or caregiver as well as the patient. These parkinsonian symptoms may also be associated with conditions other than classic Parkinson's disease.

The treatment of Parkinson's disease is based on compensating for the lack of dopaminergic neurotransmission caused by the loss of this dopaminergic population of neurons. Classically, the treatment involves the chronic oral administration of levodopa, which is able to cross the blood-brain barrier, unlike dopamine. Levodopa is a prodrug, and is decarboxylated in the brain to form dopamine. This supplementation of dopamine within the brain compensates for the degeneration of neurons that normally synthesize and release dopamine, and provides a relief from the clinical symptoms of the disease. Other drugs may also be given in conjunction with levodopa.

However, after an initial treatment period of 3–6 years, in which an optimal clinical effect of oral levodopa is observed, movement abnormalities appear in approximately 40–60% of patients. These abnormalities consist of involuntary movements during the periods of clinical improvement ("on" phases) and the re-emergence of parkinsonian symptoms at other times ("off" periods).

Several drugs that act at the postsynaptic dopamine receptor have recently been found to alleviate these abnormalities of chronic levodopa therapy and that substantially increase the duration of "on" periods of clinical improvement. The most powerful and effective of these agents, apomorphine, is limited by a short duration of action and side effects that can be circumvented by subcutaneous injection or infusion. Colosimo, C. et al., "Clinical Usefulness of Apomorphine in Movement Disorders", Clinical Neuropharmacology, 17: 243–259 (1994). However, administration of apomorphine by repeated subcutaneous injections or continuous parenteral infusion by pumps is technically difficult, especially for patients whose manual dexterity is devastated by parkinsonian symptoms and the movement abnormalities caused by chronic levodopa treatment. Oral or sublingual administration routes are unsatisfactory due to breakdown of the drug in the liver, stomatitis, and the development of buccal ulcers. No detectable plasma levels of apomorphine were produced by an attempt to administer apomorphine in a cream [Gancher, S. T. et al., "Absorption of Apomorphine by Various Routes in Parkinsonism", Movement Disorders 6(3): 212–216 (1991)].

Transdermal drug delivery devices for the continuous controlled transdermal administration of drugs other than apomorphine are well known. Examples of such devices can be found in U.S. Pat. No. 3,731,683 to Zaffaroni, U.S. Pat. No. 3,797,494 to Zaffaroni, U.S. Pat. No. 4,031,894 to Uhrquhart et al., and U.S. Pat. No. 4,336,243 to Sanvordecker et al. However, heretofore attempts to deliver apomorphine transdermally have not been successful. See, for example, Gancher et al., Ibid at p. 214.

Transdermal drug delivery devices are typically held in contact with the skin by means of a pressure-sensitive adhesive layer and are left in place for a period of 24 hours or longer.

Silicone pressure-sensitive adhesives are effective for holding such transdermal drug delivery systems to the skin for prolonged periods of time. Such silicone pressure-sensitive adhesives are known to be non-irritating and nonsensitizing to the skin, and have been used for the controlled release of nitroglycerin (Nitro-Disc®, G.D. Searle Co., Skokie, Ill.). Other transdermal drug delivery systems have been developed for the delivery of various drugs. For example, the Transderm Scop® system for the delivery of scopolamine (CIBA-Geigy, Ardsley, N.Y.) utilizes a polyisobutylene pressure-sensitive adhesive layer.

It has now been found that therapeutically effective amounts of apomorphine can be administered transdermally from an applied gel. Use of a silicone based pressure-sensitive adhesive gel matrix which maintains its tack and adherence throughout the administration of the drug provides another novel approach to the transdermal application of apomorphine.

SUMMARY OF THE INVENTION

The compositions of the present invention provide a means of sustained, reliable delivery of apomorphine in dosage forms that are easy to use and are well suited to the abilities of a patient with Parkinson's disease. In one aspect, the present invention provides an effective dose of apomorphine for amelioration of parkinsonian symptoms by means of a composition comprising a water soluble gel and apomorphine. In another aspect, the present invention also contemplates administration of apomorphine by means of a transdermal patch dosage form.

In preferred compositions of the present invention, apomorphine is present in an aqueous solution of a relatively high molecular weight polycarboxylated polymer. The polymer imparts a desirable viscous, gelled consistency to the composition when combined with apomorphine and water. The gel compositions contain at least about 40% by weight water, based on the total weight of the composition, and have the requisite degree of apomorphine concentration, hence thermodynamic activity, for effective topical delivery and bioavailability of apomorphine. The gel compositions of the present invention also have the requisite therapeutic activities for amelioration of the symptoms of Parkinson's disease.

The gel-forming polymer useful in compounding the present composition may be any suitable polymer which is hydrophilic and water-dispersible, has free carboxylic groups, and forms a gel of substantially uniform consistency.

Illustrative such polymers are the polysaccharides such as algin, xanthan, guar and the like, and synthetic hydrophilic polymers such as the alkyl celluloses, hydroxyalkyl celluloses, polyvinyl sufonates, polyacrylates, polyacrylamides and the like. Preferred polymers for use in the compositions of the invention are hydroxypropyl methylcellulose and water dispersible polycarboxylated vinyl polymers. Polyacrylic acid polymers are particularly preferred for the present purposes. The molecular weight of the polymer is desirably in the range of about 1,250,000 to about 4,000,000. Suitable polyacrylic acid polymers include, but are not limited to, polyacrylic acid polymers lightly cross-linked with a polyalkenyl polyether such as those commercially available from B. F. Goodrich, Cincinnati, Ohio, under the trademarks Carbopol 934, 940, and 941. Carbopol 934® is a particularly preferred polymer for use in practicing this invention.

The polymer is present in an amount sufficient to cause gelling of the composition and impart the desired viscous consistency to the topical formulation. The apomorphine compositions advantageously comprise about 0.1 to about 7% by weight of the polymer, preferably about 0.5% to about 1.5%, and most preferably about 1% by weight of the polymer based on the total weight of the composition.

Aqueous solutions of these polymers form gels when neutralized with a base. Water-soluble bases which may be used to promote gelling of polymers such as Carbopols™ include inorganic bases such as an aqueous solution of ammonium hydroxide, NaOH, and organic amines, e.g., alkylamines such as methylamine and ethylamine, dialkylamines, trialkylamines, alkanolamines, dialkanolamines, and the like.

The present invention contemplates drug delivery dosage forms for the administration of apomorphine in a therapeutically effective amount to a human patient. One preferred dosage form of the present invention utilizes an aqueous gel composition which contains apomorphine and a permeation enhancer therefor. Another dosage form of the present invention utilizes a pressure-sensitive medical grade silicone adhesive matrix which contains apomorphine and a permeation enhancer therefor. A therapeutically effective amount is an amount that mitigates or ameliorates parkinsonian symptoms.

A contemplated skin permeation enhancer is an aromatic or aliphatic carbocyclic compound containing pendant hydroxyl groups, such as butylated hydroxytoluene (BHT), butylated hydroxyanisole (BHA) or a hydroxypropyl-beta-cyclodextrin (HPBCD), and the like, which is present in amount up to about 30 percent by weight of the gel or the adhesive matrix.

The apomorphine is present in the dosage form of the present invention in an amount in the range of about 0.1 to about 3 percent by weight of the gel or the adhesive matrix.

A preferred transdermal patch embodying the present invention includes an occlusive backing for the adhesive matrix.

DESCRIPTION OF PREFERRED EMBODIMENTS

Figure 1:
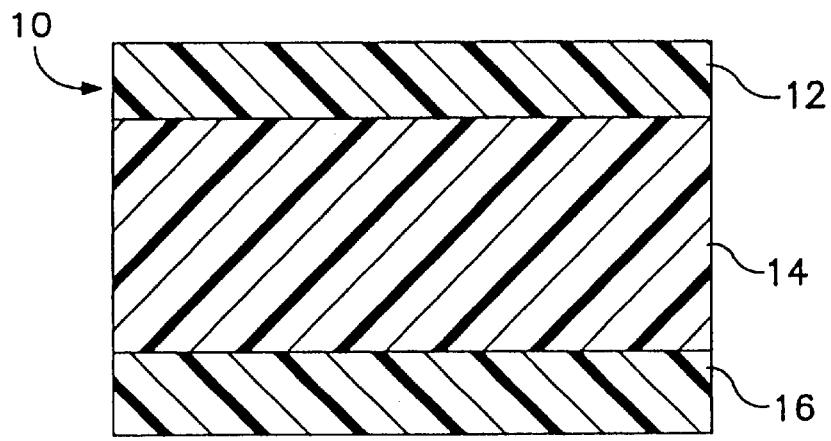
FIG. 1 shows a sectional elevation of a transdermal patch embodying the present invention.

The present invention provides an effective means for the transdermal delivery of apomorphine from a gel matrix to a patient over an extended time period. Apomorphine, an effective agonist at both dopamine receptors in the nervous system, is shown in Formula I, below.

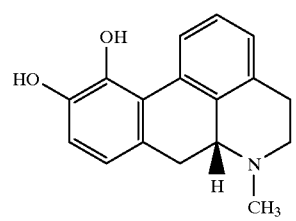

Apomorphine has recently been employed in conjunction with other medications in the treatment of Parkinson's disease patients who have become resistant to chronic levodopa therapy or who have developed abnormal movements as a consequence of chronic levodopa therapy. Apomorphine, however, has been administered by subcutaneous injections which are difficult or inconvenient for the patient. Attempts to administer apomorphine transdermally heretofore have not been effective.

The present invention, on the other hand, provides transdermal compositions and routes of application of apomorphine that are simple and convenient for the patient. Moreover, the present invention provides means for a prolonged, controlled administration of the drug.

The "therapeutically effective amount" to be delivered to a particular patient depends upon the patient's age, weight of the patient, the particular condition to be treated, and the like considerations. Apomorphine in the presently contemplated dosage forms can be administered to reduce involuntary movements and increase periods of therapeutic effectiveness ("on" periods) for patients undergoing chronic dopaminergic therapy for Parkinson's disease, parkinsonism, some forms of idiopathic dystonia, and other disorders. A "permeation enhancer" as used herein is a compound compatible with apomorphine that facilitates the uptake of apomorphine through the skin and thus enables a therapeutically effective dosage of apomorphine to be administered to the patient.

The presently contemplated permeation enhancers are aromatic or aliphatic carbocyclic compounds that have pendant hydroxyl groups, such as butylated hydroxytoluene (BHT), butylated hydroxyanisole (BHA), and hydroxypropyl-beta-cyclodextrin (HPBCD), and the like, as well as mixtures thereof.

The permeation enhancers of the present invention increase the permeability of the treated area of skin to apomorphine to a magnitude such that sufficient apomorphine is absorbed to provide a therapeutically effective level of apomorphine in the bloodstream. The rate of permeation enhancer administration is controlled by its rate of release from the water-soluble gel, or the adhesive matrix of a transdermal patch, to the skin surface. Thus the rate of apomorphine administration is correlated with the concurrent rate of release of the permeation enhancer, since the permeation enhancer modulates the rate at which the skin absorbs the apomorphine.

II

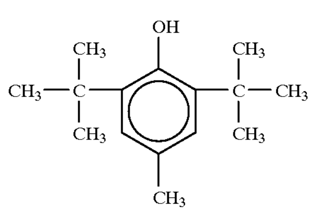

-continued

III

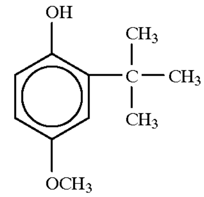

Preferred permeation enhancers are BHT, BHA and HPBCD, represented by Formulas II, III and IV, respectively. BHT and BHA are commercially available compounds that are insoluble in water but soluble in organic solvents.

Hydroxypropyl-beta-cyclodextrins are commercially available compounds that are derived from beta-cyclodextrins by condensation with a propylene oxide to provide the corresponding hydroxypropyl derivatives having a degree of substitution (D.S.) up to about 15 or higher. For the purposes of the present invention a D.S. value of about 5 to 7 is preferred.

IV

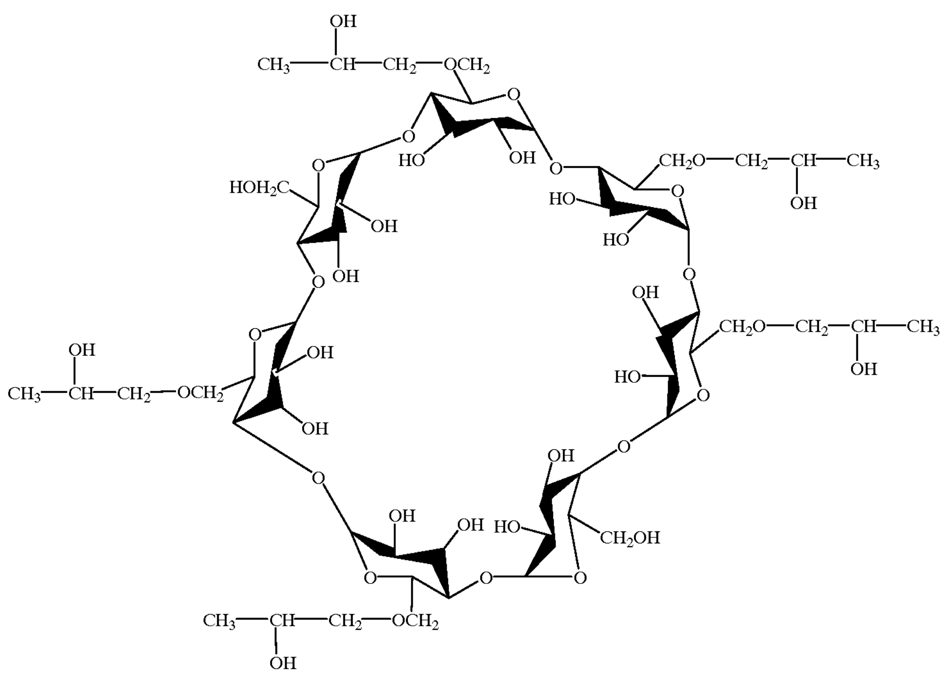

The preparation of suitable hydroxypropyl-beta-cyclodextrins is described, inter alia, in International Journal of Pharmaceutics 29: 73–82 (1986) and in Journal of Pharmaceutical Sciences 75(6): 571–572 (1986). Also known, and contemplated for the purposes of the present invention, are the hydroxypropyl-beta-cyclodextrins that are polyethers of cyclodextrins and are obtained by condensation of an excess of hydroxypropylene oxide with beta-cyclodextrin as described in U.S. Pat. No. 3,59,731 to Gzamera et al.

A preferred topical vehicle for apomorphine is a water-soluble, nonirritating gel that does not sensitize the skin. In a particularly preferred embodiment of the present compositions, the topical vehicle has a semi-soft consistency. This can be obtained by the use of a water-soluble gel such as hydroxypropylmethylcellulose, and the like materials. A suitable methylcellose is commercially available under the designation of Methocel E4M. Alternatively, an acrylic acid polymer can be used to obtain a topical gel vehicle of the desired consistency. A suitable acrylic acid polymer for this purpose when neutralized is a Carbopol®-type gel such as Carbopol® 934P. The weight percent of the gel-forming polymer in the present composition is in the range of about 0.1 to about 7. Illustrative compositions are shown in Tables I & II, below.

Improved results are obtained by the use of hydroxypropyl-beta-cyclodextrin (HPBCD) in the composition. HPBCD is a cyclic polymer having a doughnut-shaped molecular structure including an inner cavity. While the mechanism is not clear, it is believed that an inclusion compound is formed with the HPBCD. This makes the resulting moiety more readily absorbed by the skin. While HPBCD is the preferred cyclodextrin constituent, other cyclodextrins can also be used. The weight percent of the HPBCD in the composition is preferably in the range of about 1 to about 10.

It is preferable that the pH of the composition be in the range of about 7 to about 8, preferably 7.4, to maximize the availability of the free base form of the apomorphine and thus to maximize skin absorption. Ammonium hydroxide or sodium hydroxide can be used to adjust the pH of the topical vehicle.

The remaining components of the composition are water and monohydric and polyhydric alcohols such as ethanol, polyethylene glycol and propylene glycol. The weight percent of water in the composition is in the range of about 20 to about 80, and that of the alcohols about 80 to about 40. Ethanol and propylene glycol preferably are present in a relative weight ratio of about 3:1 to about 0.1:1.

Ascorbic acid, citric acid, phosphoric acid, glutathione, and the like can be added to the present compositions to enhance the stability thereof. The tocopherols, such as d-alpha-tocopherol (Vitamin E), also are suitable stabilizers for the present compositions.

In a preferred embodiment, a permeation enhancer can be present up to about 20 percent by weight of the patch composition in a transdermal patch of the present invention and increases the rate of apomorphine permeability into skin at a rate that is at least comparable to the rate of release of apomorphine from the adhesive matrix.

A contemplated dosage form of the present invention is a transdermal patch in which the pressure-sensitive adhesive matrix provides contact with the skin surface of a patient and acts as a reservoir of apomorphine, permitting the apomorphine present to permeate into the skin surface of a mammal at a therapeutically effective rate. The amount of apomorphine present is in the range of about 0.1 to about 3 weight percent, preferably about 0.1 to about 0.3 percent, based on the weight of the adhesive matrix.

The concentration of the permeation enhancer varies based on the specific permeation enhancer utilized. In one embodiment, when the permeation enhancer is BHT, it is present in an amount in the range of about 0.1 to about 5 percent by weight of the adhesive matrix, preferably about 0.5 to about 1.0 percent by weight of the adhesive matrix. When a hydroxypropyl-beta-cyclodextrin is used as the permeation enhancer, it is present in an amount in the range of about 1 to about 20 percent by weight of the adhesive matrix, and preferably about 1 to about 10 percent by weight of the adhesive matrix. The weight ratio of apomorphine-to-BHT is in the range of about 20 to about 0.05, preferably about 3 to about 0.1, and the weight ratio of apomorphine-to-HPBCD is in the range of about 20 to about 0.1.

FIG. 1 illustrates a preferred discoid dosage form 10 in which a pressure-sensitive silicone adhesive matrix 14 containing apomorphine and a permeation enhancer therefor is sandwiched between an occlusive backing 12 and a release liner 16. Occlusive backing 12 is a film usually having a thickness of about 2.5 to about 3 mils. Release liner 16 likewise has a usual thickness of about 2.5 to about 3 mils. The thickness of adhesive matrix 14 usually is about 10 mils. Removal of release liner 16 typically exposes a pressure-sensitive adhesive matrix surface of about 7 $cm^2$ across which a flux of apomorphine is delivered to a patient when the exposed adhesive surface is placed in intimate contact with the patient's skin.

The adhesive matrix preferably is constituted by a medical grade pressure-sensitive silicone adhesive of the type shown in FIG. 2, such as BIOPSA (g) Q7-2920 [Structure (ii) when y is 500 to 1000], commercially available from Dow Corning Corporation, Midland, Mich. 48640, in a cyclohexane medium, and an aromatic or aliphatic carbocyclic permeation enhancer for apomorphine as described hereinabove.

Figure 3:
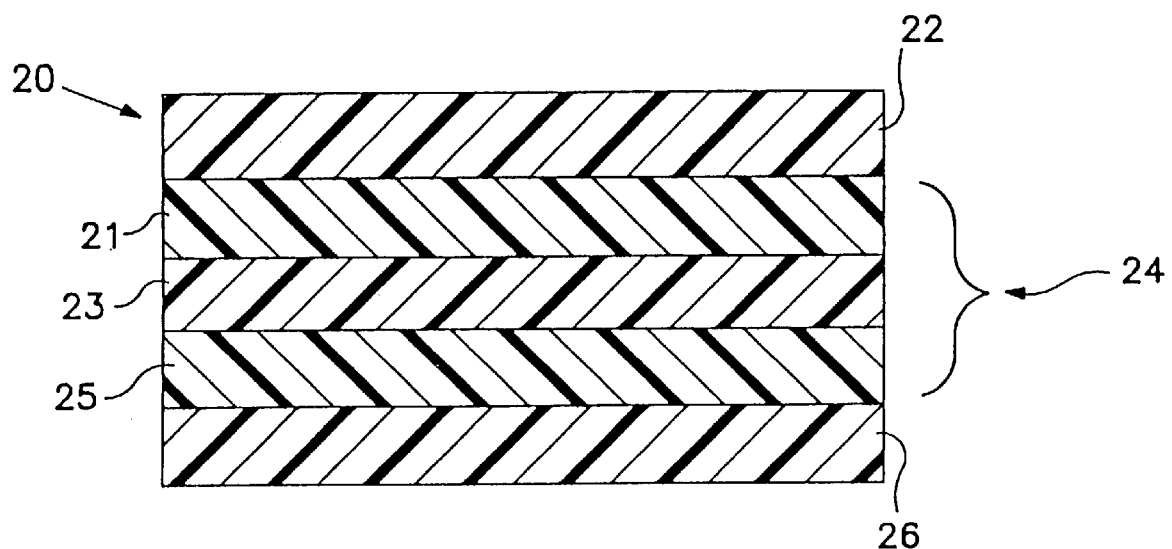
FIG. 3 shows a sectional elevation of a multilayered transdermal patch embodying the present invention.

In another embodiment, a dosage form of the present invention is a multilayered discoid patch in which the concentration of apomorphine and permeation enhancer in the adhesive matrix varies in adjacent layers. FIG. 3 illustrates an exemplary multilayered dosage (20) form of the present invention in which a pressure-sensitive adhesive matrix 24 composed of three independent layers 21, 23 and 25, respectively, containing apomorphine and a permeation enhancer therefor is sandwiched between an occlusive backing 22 and a release liner 26. The occlusive backing 22 and release liner 26 are as described for FIG. 1, hereinabove. The thickness of the adhesive matrix 24 is about 10 to about 20 mils. In a preferred embodiment a dosage form of the present invention has a skin contact adhesive layer containing a relatively high concentration of a permeability enhancer such as BHT and a relatively low concentration of apomorphine. Successive additional adhesive layers are placed upon the preceding layer, where each successive layer has a relatively lower concentration of permeation enhancer and a relatively higher concentration of apomorphine present. The apomorphine concentration in a adhesive matrix layer is about 0.1 to about 10 percent by weight of the layer. The total amount of the apomorphine present in all the layers is in an amount from about 0.1 to about 1 percent by weight of adhesive matrix. An occlusive backing layer is present as the top layer of the dosage form.

Several variations of the transdermal dosage form of the present invention are contemplated.

Illustrative dosage forms of the present invention include those in which the adhesive matrix between the occlusive backing film (BF) and the release liner on the skin contact surface (RL) is composed of a plurality of individual layers containing, in addition to the silicone pressure-sensitive adhesive, differing concentrations of permeation enhancer (PE) and/or apomorphine sufficient to form a step gradient of the respective components in the dosage form. Exemplary dosage forms include the following, where the virgule (/) represents the interface between individual layers and a series of three dots ( . . . ) indicates a plurality of intermediate layers of either successively increasing or successively decreasing concentrations of the active component(s) present in the adhesive matrix. In other words, the amount of apomorphine and permeation enhancers is different in each layer. Additionally, a matrix can be present that contains neither apomorphine nor a permeation enhancer therefor. Listed below, schematically, as progressing from a relatively "Higher" to a relatively "Lower" concentration, or vice versa, are the following illustrative dosage forms:

(a) [RL]/[Higher PE only]/[PE & Lower apomorphine] . . . [PE & Higher apomorphine]/[BF];
(b) [RL]/[PE & Lower apomorphine] . . . [PE & Higher apomorphine]/[BF];
(c) [RL]/[Higher PE] . . . [Lower PE only]/[matrix only]/ [Lower apomorphine only] . . . [Highest apomorphine]/ [BF]; and
(d) [RL]/[Higher PE & apomorphine] . . . [Lower PE & apomorphine]/[matrix only]/Lower apomorphine only] . . . [Higher apomorphine]/[BF].

A dosage form, as described above, is also contemplated that contains different permeation enhancers in contiguous independent layers of the adhesive matrix. In one embodiment, a transdermal patch is contemplated containing an occlusive backing layer coextensive with a two-layer adhesive matrix. In this embodiment, the adhesive matrix is composed of a first layer coextensive with the backing layer and containing apomorphine and a HPBCD together with the silicone adhesive, and a second layer contiguous with the first layer and containing apomorphine and BHT together with the silicone adhesive. In a second embodiment a transdermal patch having a three-layer adhesive matrix contiguous to an occlusive backing layer is contemplated in which each layer of the matrix is composed of a silicone adhesive and, in addition, the first layer contains apomorphine and a HPBCD, the second layer contains apomorphine and BHT, and the third layer contains BHT alone. Silicone pressure-sensitive adhesive compositions preferred for use in practicing the present invention are described in U.S. Pat. Nos. 4,591,622 to Blizzard et al.; 4,594,355 to Blizzard et al.; 4,585,836 to Homan et al.; and 4,655,767 to Woodard et al. The disclosures of the foregoing patents are incorporated herein by reference to the extent pertinent. Illustrative pressure sensitive silicone adhesives suitable for use in a transdermal drug delivery system are those described in Pfister, W. R., Pharmaceutical Technol. 13: 126–138 (1989), whose disclosure is incorporated herein by reference.

An illustrative silicone pressure-sensitive composition is prepared as described hereinafter. About 40 to about 70 parts by weight of at least one benzene soluble resin copolymer containing silicon-bonded hydroxyl radicals and consisting essentially of $R_3SiO_{1/2}$ units and $SiO_{4/2}$ units in a mole ratio of 0.6 to 0.9 $R_3SiO_{1/2}$ units for each $SiO_{4/2}$ unit present (Component A), about 30 to about 60 parts by weight of at least one polydiorganosiloxane consisting essentially of ARSiO units terminated with endblocking $TRASiO_{1/2}$ units, each said polydiorganosdoxane having a viscosity of from 100 centipoise to 30,000,000 centipoise at 25° C., where each T is R— or X— (Component B), a sufficient amount of at least one organosilicone endblocking agent capable of generating an endblocking triorganosilyl unit selected from the group consisting of $ZR_2Si$— units, $CH_3Z'$— units and $RZ"$— units and $Z"'R_2Si$— units to provide a 1:0.8 to 1:3 mole ratio of total silicon-bonded hydroxyl and X radicals present in Components A and B to total endblocking triorganosilyl units provided by all endblocking blocking agent present, said agent being selected from the group consisting of $ZR_2SiY$, $(ZR_2Si)_qD$, $CH_3Z'Y$, $(CH_3Z')_2O$, $RZ"Y'$, $(RZ")_2O$ and $Z"'R_2SiY'$ (Component C), an additional catalytic amount of a mild silanol condensation catalyst (Component D) in the event that none is provided by Component C, are admixed together with an organic solvent which is inert with respect to Components A, B, C, and D in an amount sufficient to reduce the viscosity of the resulting admixture, and this admixture is condensed at least until a substantial amount of the endblocking triorganosilyl units have reacted with the silicon-bonded hydroxyl radicals and X radicals of Components A and B.

In the aforementioned components, each R is a monovalent organic radical selected from the group consisting of hydrocarbon radicals of from 1 to 6 inclusive carbon atoms, each X radical is selected from the group consisting of HO—, H—and R'O— radicals, each R' is an alkyl radical of from 1 to 4 inclusive carbon atoms, each Y radical is a monovalent hydrolyzable organic radical or HO—, each Y' is HO— or a monovalent hydrolyzable organic radical free of nitrogen, each A radical is selected from the group consisting of R— and halohydrocarbon radicals of from 1 to 6 inclusive carbon atoms such as chloromethyl, chloropropyl, 1-chloro-2-methylpropyl, 3,3,3-trifluoropropyl and $F_3C(CH_2)_5$—, each Z radical is A— or QR"—, each R" is a divalent alkylene radical of from 1 to 6 inclusive carbon atoms, each Q is an organofunctional monovalent radical selected from the group consisting of RCOE'—, RE'OC—, NC—, R'E'—, HO—, $G_2N$—, $HO(R")_n$—, and $G_2NCH_2CH_2NG$—, where E' is —O—, —NG— or —S—, n has a value of from 1 to 6,

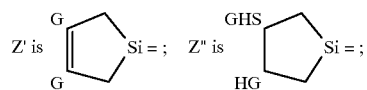

Z"'is selected from the group consisting of HSR"—, $HSCH_2CH_2NGR"$— and $HOCH_2CH_2SR"$— radicals, each G is R'— or H—, D is a divalent or trivalent organic capable of being hydrolyzed to release said endblocking silyl units and q has a value of 2 when D is a divalent radical and q has a value of 3 when D is a trivalent radical. Exemplary R groups include methyl, ethyl, propyl, isopropyl, hexyl, cyclohexyl, vinyl, allyl, propenyl and phenyl. Preferably, the $R_3SiO_{1/2}$ units are $Me_2R"'SiO_{1/2}$ units wherein R"" is a methyl ("Me"), vinyl ("Vi") or phenyl ("Ph") radical. More preferably, no more than 10 mole percent of the $R_3SiO_{1/2}$ units present in Component A are $Me_2R""SiO_{1/2}$ units and the remaining units are $Me_3SiO_{1/2}$ units where each R"" is a methyl or a vinyl radical.

More preferred are compositions employing about to about 65 parts by weight of Component A and about 35 to about 50 parts by weight of Component B. For low tack adhesives, compositions having about 58 to about 65 parts by weight of Component A and about 35 to about 42 parts by weight of Component B are utilized.

The benzene-soluble silicone resin copolymers that constitute Component A are well-known materials. They contain silicon-bonded hydroxyl radicals in amounts which typically range from about 1 to 4 weight percent of silicon-bonded hydroxyl radicals and consist essentially of triorganosiloxy units of the formula $R_3SiO_{1/2}$ and tetrafunctional siloxy units of the formula $SiO_{4/2}$ in a mole ratio of from 0.6 to 0.9 $R_3SiO_{1/2}$ units for each $SiO_{4/2}$ unit present. Blends of two or more such copolymers may also be used. There should be at least some and preferably at least 0.5% silicon-bonded hydroxyl content to enable the polydiorganosiloxane component to copolymerize with the copolymer resin and/or to react with the endblocking agent being added to chemically treat the silicone pressure-sensitive adhesive composition. These resin copolymers are benzene-soluble resinous materials which are typically solids at room temperature and are prepared as, and usually, but not necessarily used as, a solution in an organic solvent. Typical organic solvents used to dissolve Component A include benzene, toluene, xylene, methylene chloride, perchloroethylene, naphtha mineral spirits and mixtures of these.

A few mole percent of $R_2SiO$ units can be present in Component A if the presence of such units does not cause the ultimate product to lose its ability to function as a pressure-sensitive adhesive.

The mole ratio of $R_3SiO_{1/2}$ and $SiO_{4/2}$ units can be determined simply from a knowledge of the identity of the R radicals in the $R_3SiO_{1/2}$ units and the present carbon analysis of the resin copolymer. In the preferred resin copolymer having from about 0.6 to about 0.9 $Me_3SiO_{1/2}$ units for every $SiO_{4/2}$ unit, the carbon analysis has a value of from about 19.8 to about 24.4 percent by weight.

Component A may be prepared according to U.S. Pat. No. 2,676,182 to Daudt et al. (hereby incorporated by reference) whereby a silica hydrosol is treated at a low pH with a source of $R_3SiO_{1/2}$ units such as a hexaorganosiloxane such as $Me_3SiOSiMe_3$, $ViMe_2SiOSiMe_2Vi$ or $MeViPhSiOSiPh-ViMe$ or triorganosilane such as $Me_3SiCl$, $Me_2SiCl$ or MeViPhSiCl. Such copolymer resins are typically made such that the copolymer resin contains about 1 to about 4 weight percent of silicon-bonded hydroxyl radicals. Component B is also a well-known material and is one or more polydiorganosiloxanes containing ARSiO units terminated with endblocking $TRASiO_{1/2}$ units, each of which polydiorganosiloxanes has a viscosity of from about 100 centipoise to about 30,000,000 centipoise at 25° C. (about 100 millipascal seconds to about 30,000 pascal seconds (Pa.s) where 1 centipoise equals 1 millisecond). As is well-known, viscosity is directly related to the average number of diorganosiloxane units present for a series of polydiorganosiloxanes of varying molecular weights which have the same endblocking units. Polydiorganosiloxanes having a viscosity of from about 100 to 100,000 centipoise at 25 degrees C. range from fluids to somewhat viscous polymers. These polydiorganosiloxanes are preferably pre-reacted with Component A prior to condensation in the presence of Component C to improve the tack and adhesion properties of the resulting pressure-sensitive adhesive as will be further described. Polydiorganosiloxanes having viscosities in excess of 100,000 centipoise can typically be subjected to the condensation and endblocking as described above. Polydiorganosiloxanes having viscosities in excess of 1,000,000 centipoise are highly viscous products often referred to as gums and the viscosity is often expressed in terms of a Williams Plasticity value. Polydimethylsiloxane gums of about 10,000,000 centipoise viscosity typically have a Williams Plasticity value of about 50 mils (1.27 mm) or more at 25° C.

Component B contains ARSiO units where each R and A, respectively are as defined above. Thus the polydiorganosiloxane can contain $Me_2SiO$ units, PhMeSiO units, MeViSiO units, $Ph_2SiO$ units, methylethylsiloxy units, 3,3,3-trifluoropropyl units and 1-chloro-2-methylpropyl units and the like. Preferably, the ARSiO units are selected from the group consisting of $R_2'''SiO$ units, $Ph_2SiO$ units and combinations of both where R''' is as above. At least 50 mole percent of the R''' radicals present in Component B are methyl radicals and no more than about 50 mole percent of the total moles of ARSiO units present in Component B are $Ph_2SiO$ units. More preferably, no more than 10 mole percent of the ARSiO units present in Component B are MeR''''SiO units where R'''' is as above defined and the remaining ARSiO units present in each polydiorganosiloxane are $Me_2SiO$ units.

Each polydiorganosiloxane of Component B is terminated with endblocking units of the unit formula $TRASiO_{1/2}$ where R and A are as defined above and each T radical is R or X wherein each X radical is selected from HO—, H— and R'O— radicals, where each R' is an alkyl radical of from 1 to 4 inclusive carbon atoms such as methyl, ethyl, n-propyl, and isobutyl radicals. The X radicals provide a site for reaction with the endblocking triorganosilyl units of Component C and also provide a site for condensation with other X radicals on Component B or with the silicon-bonded hydroxyl groups present in Component A. Use of polydiorganosiloxanes where T is HO— is most preferred because the polydiorganosiloxane of Component B can then readily copolymerize with the resin copolymer Component A. When appropriate catalysts such as HCl or ammonia are used as endblocking agents, triorganosiloxy (e.g., $R_3SiO_{1/2}$ such as $(CH_3)_3SiO_{1/2}$ or $CH_2=CH(CH_3)_2SiO_{1/2})$ unit terminated polydiorganosiloxanes can be employed because some of the triorganosiloxy units can be cleaved when the condensation reaction is conducted with heating. The cleavage exposes a silicon-bonded hydroxyl radical which can then condense with silicon-bonded hydroxyl radicals in the copolymer resin, with endblocking triorganosilyl units or with other polydiorganosiloxanes containing X radicals or silicon-bonded hydroxyl radicals exposed by cleavage reactions. Mixtures of polydiorganosiloxanes containing different substituent radicals may also be used.

Methods for the manufacture of such polydiorganosiloxanes are well known as exemplified by U.S. Pat. Nos. 2,490,357 to Hyde; 2,542,334 to Hyde; 2,927,907 to Polmanteer, 3,002,951 to Johannson; 3,161,614 to Brown, et al.; 3,186,967 to Nitzche, et al.; 3,509,191 to Atwell and 3,697,473 to Polmanteer, et al. which are hereby incorporated by reference.

One embodiment of the dosage form of the present invention is a transdermal patch that contains an occlusive backing layer attached to the adhesive matrix on a face opposed to the surface capable of adhesively contacting a skin surface, and a release liner attached to the skin contact surface of the adhesive matrix.

Figure 2:
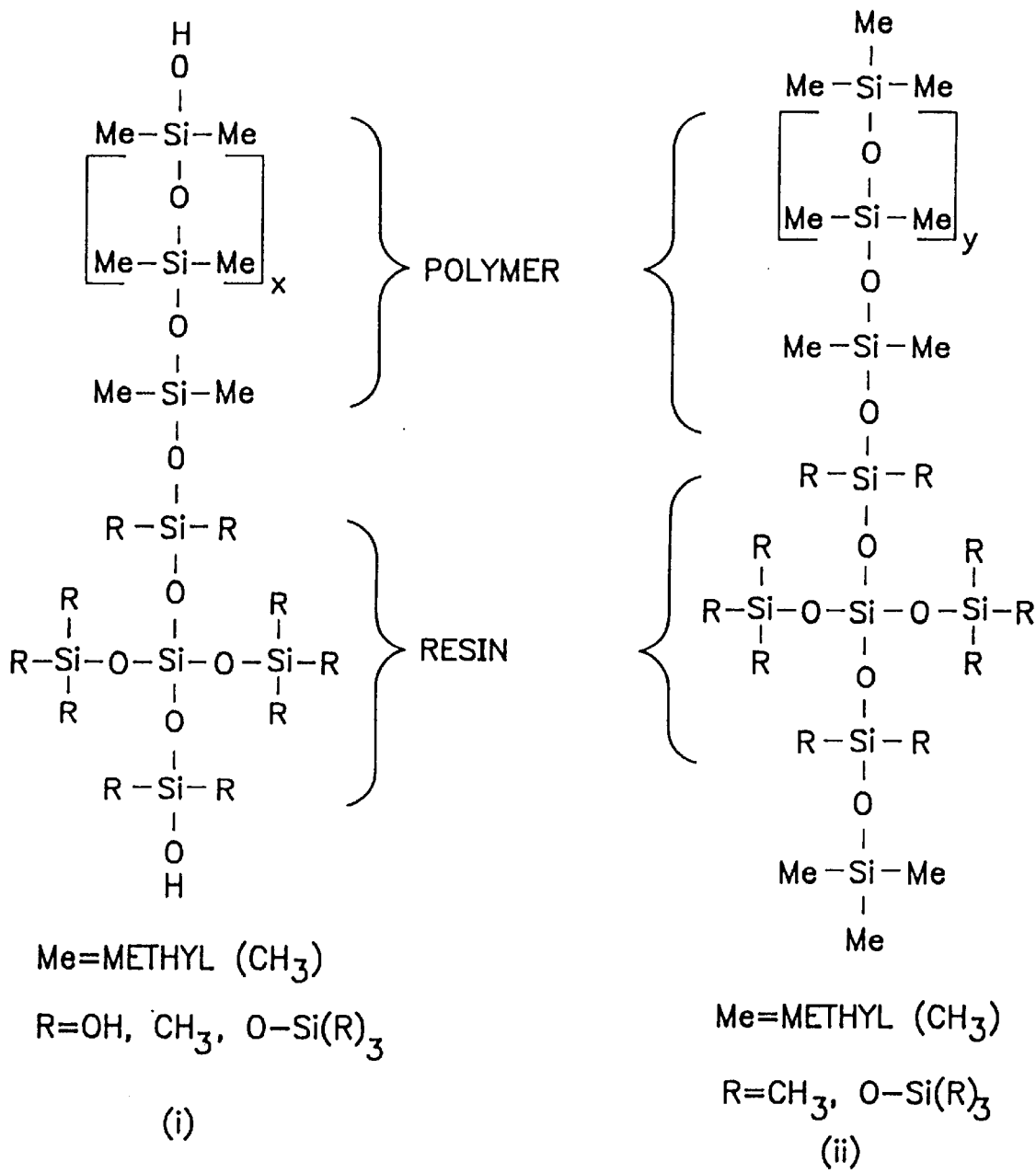
FIG. 2 shows the structures for two pressure-sensitive dimethyl silicone adhesives which are effective in the present invention. Replacement of the hydroxyl groups in Structure (I) with trimethyl siloxyl groups produce an amine-resistant silicone adhesive shown as Structure (II). Values for x and y are in the range of about 500 to about 1000.
Figure 4:
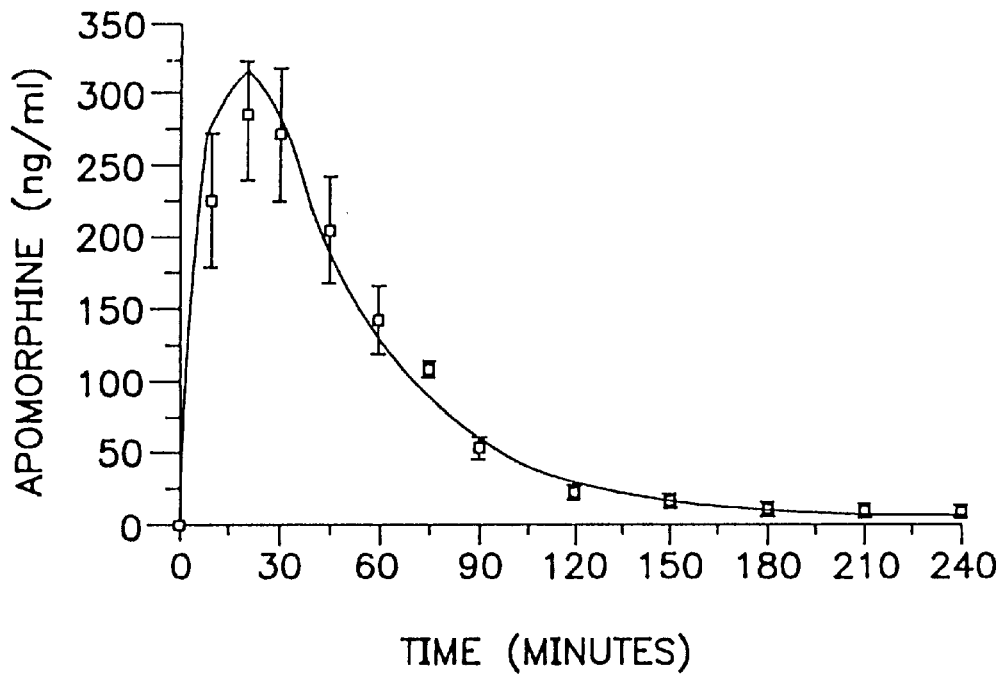
FIG. 4 shows the time course of transdermal permeation of apomorphine from a gel preparation determined in vitro using human skin.

The adhesive matrix in this particular embodiment contains the pressure-sensitive medical-grade silicon adhesive, shown in FIG. 2 as Structure (ii), a permeation enhancer and apomorphine. The adhesive matrix can contain a plurality of layers where each successive layer contains in addition to the adhesive varying concentrations of apomorphine and/or a permeation enhancer. The occlusive backing layer is a polyester film [SCOTCHPAK® 1006 Film (3M Co., St. Paul, Minn.)]. The release liner is another polyester film [SCOTCHPAK® 1022 Film (3M Co., St. Paul, Minn.)], provided with a release surface.

In a particularly preferred embodiment, the transdermal patch has an adhesive matrix containing butylated hydroxytoluene (BHT) and apomorphine, attached to an occlusive SCOTCHPAK® 1006 Film backing layer. The transdermal patch is attached to the skin of a patient by contacting the skin with the adhesive.

The gels and the transdermal patch of the present invention are useful in the treatment of Parkinson's disease, parkinsonism and other disorders treated by chronic dopaminergic therapy. The continuous administration of apomorphine to a patient produces a substantial improvement in therapeutic effectiveness ("on" time) and minimizes side-effect movement disorders.

Application of apomorphine gel as a topical composition or as a transdermal patch of the present invention to the skin of a patient allows a predetermined amount of apomorphine to be administered continuously to the patient and thus avoids the inconvenience of subcutaneous injections and undesirable effects present with single or multiple administration of larger apomorphine dosages. By maintaining a sustained dosage rate, the apomorphine level in the patient's blood can be continuously maintained within the optimal therapeutic range.

The present invention is further illustrated by the following EXAMPLES.

EXAMPLE 1

Apomorphine Gel Preparation

Preparation of the Topical Vehicle

The desired amount of the acrylic acid polymer is weighed and dispersed in about one-half the final amount of water. The pH of the resulting dispersion is adjusted to a pH of about 7 to about 8 using ammonium hydroxide. The resulting composition is maintained at about ambient temperature for about 18 hours to obtain the desired viscous consistency.

Preparation of a Solution of Active Ingredients

The desired amount of apomorphine is weighed and dissolved in the total amount of ethanol and propylene glycol. Ascorbic acid is also added as an anti-oxidant. The desired amount of HPBCD is weighed and dissolved it in the remaining amount of water. The obtained aqueous HPBCD solution is combined with the alcoholic solution of the apomorphine and the aforementioned optional ingredients; and the pH of the combined solutions is adjusted with ammonium hydroxide to a value of about 7 to about 8. The combined solutions containing the active ingredients are further admixed with the prepared topical vehicle to form the composition.

One example of such a composition is a 4% hydroxypropyl-methylcellulose gel containing apomorphine HCl at 10 mg/g and ascorbic acid at 2 mg/g. Hydroxypropyl-methylcellulose (USP XXII, 0.04 g) is added slowly with stirring to purified water (60° C., sufficient to yield a total of 1 g) and stirred until completely dissolved. When the hydroxypropyl-methylcellulose is completely dissolved, the gel is cooled in a refrigerator or on an ice bath until it reaches room temperature. The gel is then weighed. Appropriate amounts of apomorphine and ascorbic acid are added with stirring to yield final concentrations of apomorphine HCl at 10 mg/g and ascorbic acid at 2 mg/g.

The preferred topical apomorphine gel compositions disclosed herein contain HPBCD. In the gel compositions, the weight percent of HPBCD exceeds the weight percent of apomorphine. Table I enumerates several compositions, some that contain HPBCD and some that do not. Those that contain HPBCD are examples of the preferred compositions. Those compositions that do not contain HPBCD are used to illustrate the advantages of HPBCD-containing composition in the following examples.

The topical apomorphine gels in Table II are made according to the following detailed procedure. Distilled water (164 g) was added to a beaker and heated to about 50° C. to about 60° C. while the water was stirred. Methocel E4M (16.5 g) was slowly added to the solution while mixing. The solution was then cooled while being mixed for about 15 minutes in an ice bath, to a temperature of about 10° C. to about 15° C. Hydroxypropyl-beta-cyclodextrin (HPBCD) (16.5 g) was mixed with ethanol (70 g). The mixture was stirred for about 10–15 minutes until the HPBCD was completely dissolved.

An apomorphine solution was prepared by adding apomorphine (5.5 g) to ethanol (177.5 g). The resulting mixture was stirred and heated to a temperature of about 50° C. to about 60° C. until the apomorphine was completely dissolved. The HPBCD and apomorphine solutions were combined and stirred for about 5 minutes. The combined solution was then mixed with the above Methocel solution using a high torque stirrer for at least 15 to 20 minutes. The resulting mixture was packaged in small tubes (5 g per tube).

TABLE I

Representative Topical Apomorphine Gels

| Ingredients (wt. %) | Gel Preparation FORMULA | | | | | | |
|---|---|---|---|---|---|---|---|
| | A | B | C | D | E | F | G |
| Apomorphine HCl | 0.3 | 0.3 | 0.3 | 0.3 | 0.3 | 0.3 | 0.3 |
| HPBCD | 1.0 | 0 | 1.5 | 1.0 | 0 | 1.0 | 1.0 |
| Ethanol | 35.0 | 30.0 | 30.0 | 35.0 | 35.0 | 35.0 | 35.0 |
| Methocel E4M | 2.0 | 2.0 | 1.5 | 0 | 0 | 0 | 0 |
| Carbopol 934P | 0 | 0 | 0 | 1.0 | 1.0 | 1.0 | 1.0 |
| NH$_4$OH, q.s. (pH) | pH 7–8 | pH 7–8 | pH 7–8 | pH 7–8 | pH 7–8 | pH 7–8 | pH 7–8 |
| Water | 39.7 | 69.7 | 39.7 | 40.7 | 40.7 | 40.7 | 40.7 |
| Methanol | 0 | 1.0 | 0 | 0 | 1.0 | 0 | 0 |
| Propylene Glycol | 15.0 | 20.0 | 20.0 | 15.0 | 15.0 | 15.0 | 15.0 |
| Total (%) | 100 | 100 | 100 | 100 | 100 | 100 | 100 |

TABLE II

Representative Topical Apomorphine Gels

| Ingredients (wt. %) | Gel Preparation | | | | |
|---|---|---|---|---|---|
| | Formula 1 | Formula 2 | Formula 3 | Formula 4 | Formula 5 |
| Apomorphine HCl | 0.1 | 0.1 | 0.2 | 0.2 | 0.2 |
| HPBCD | 1.5 | 0 | 3 | 0 | 3 |
| Ethanol | 20 | 10 | 20 | 10 | 20 |
| Methocel E4M | 2 | 2 | 2 | 2 | 2 |
| NH$_4$OH, q.s. (pH) | pH 7–8 | pH 7–8 | pH 7–8 | pH 7–8 | pH 7–8 |
| Water | 76 | 77 | 74 | 76 | 64 |
| Propylene Glycol | 0 | 10 | 0 | 10 | 10 |
| Total (%) | 100 | 100 | 100 | 100 | 100 |

EXAMPLE 2

Flux of Apomorphine Across Human Skin

Human skin samples were obtained from white female patients undergoing breast reduction surgery and prepared for in vitro permeation studies. Samples were stratum corneum from breasts of patients 21 years (Sample A) years old and 20 years old (Samples B & C). A 2.0 cm$^2$ section of the skin tissue was placed in a Franz cell holder and maintained under phosphate buffered saline (PBS: 0.01M phosphate, 0.9% NaCl, pH 6.0) until testing. PBS (6.8 to 7.3 ml) was placed on the receptor side of the Franz cell. Apomorphine gel (Formula B of Table I, 275–343 mg, to which was added 50 µl of 50% phosphoric acid to stabilize the apomorphine) was added to the donor side of the Franz cell. The cell was incubated at 35±1° C. A 250 µl sample was taken from the receptor medium at the following times: 0, ½, 1, 2, 4, and 6 hours. An equal volume of PBS was replaced each time a sample was withdrawn.

Apomorphine levels were determined by High-performance Liquid Chromatography (HPLC) with UV (274 nm) detection. Samples were pre-filtered (0.45 µm) prior to injection. Samples (50 µl) were injected on an Altima (Alltech Associates) C18 column (15 cm×4.3 mm) with guard column. The mobile phase consisted of a 60:40 mixture of 5 mM sodium dodecylsulfate in 1 mM $NH_4PO_4$ buffer, pH 3.0 and acetonitrile. The reference standard was USP apomorphine HCl, Lot #F-1.

The results are shown in Table III.

TABLE III

In vitro Transdermal Permeation of Human Skin by Apomorphine HCl

| SAMPLE | TIME (Hours) | | | | | | FLUX |
| --- | --- | --- | --- | --- | --- | --- | --- |
| | 0 | 0.5 | 1 | 2 | 4 | 6 | $\mu g/cm^2/hr$ |
| A | 0 | 0 | 0.76 | 0.40 | 2.09 | 1.61 | 0.42 |
| B | 0 | 1.32 | 5.39 | 8.15 | 19.0 | 15.8 | 4.21 |
| C | 0 | 0 | 0 | 0.23 | 0 | 1.50 | 0.20 |
| AVERAGE | 0 | 0.44 | 2.05 | 2.93 | 7.03 | 6.30 | 1.61 |

EXAMPLE 3

Comparison Between Percutaneous and Subcutaneous Administration of Apomorphine

A pharmacokinetic comparison between percutaneous and subcutaneous administration of apomorphine was made using rabbits. Male albino rabbits (Charles River, France) (2.5–4.7 kg) were individually housed in standard laboratory conditions with free access to food and water.

Drugs: Subcutaneous Route

Apomorphine hydrochloride (Apokinon, a trademark of Aguettant Laboratory, France) was injected in the interscapular region (0.5 mg/kg).

Drugs: Percutaneous Route

An apomorphine gel was prepared in the 24 hours before the experiment by dissolving apomorphine hydrochloride (Sanofi Laboratory, France) in an hydroxypropylmethylcellulose gel of medium viscosity (Metalose 4000, Seppic, France). Apomorphine concentration was 10 mg per g of gel. Ascorbic acid (2 mg/g of gel) was added to ensure the stability of apomorphine. After removal of the hair, performed at least 24 hours before the experiment, 0.5 mg/kg of apomorphine gel (apomorphine hydrochloride, 0.5 mg/kg) was placed on the skin of the interscapular region and covered with a transparent film (Tegaderm, a trademark of 3M Laboratory, France). Six hours after, all the system was removed and the skin was washed.

All animals were anesthetized with etomidate (0.1 mg/kg i.v.)+flunitrazepam (0.1 mg/kg i.v.) before implantation of a cannula into the right vena cava via the jugular vein. Blood samples were obtained from awake animals, before and at different times (10, 20, 30, 45, 60, 90, 120, 180, 210, and 240 minutes) after the apomorphine administration for the two routes and after some supplementary times (300, 360, 390, 420 and 450 minutes) for the percutaneous administration only. Blood samples were collected in heparinized tubes which were protected from light and heat. Immediately after centrifugation (4000×gravity, 10 minutes) the plasma was recovered and collected in tubes containing ethylenediamine tetra acetic acid (EDTA) (0.1 g/ml, 100 $\mu$l/ml of plasma) and ascorbic acid (1 mg/ml, 50 $\mu$l/ml of plasma) and, after shaking, was frozen at −80° C. until analysis.

Apomorphine levels were determined by HPLC with electrochemical detection. Immediately after thawing and before plasma extraction, 100 $\mu$l of EDTA solution containing internal standard [propylnorapomorphine (NPA) Research Biochemicals, Inc, MA, USA] was added to 0.5 ml of plasma. Extraction was carried out by shaking the mixture for 10 minutes with 2 ml of ethyl acetate. After centrifugation (10,000×gravity for 10 minutes), the organic layer was back-extracted with 0.3 ml of 0.1 M hydrochloric acid. Finally, the aqueous phase was injected upon the HPLC system. Separations were carried out on a Lichrosorb CN column (250×4.7 mm i.d.). The mobile phase was 75 mM sodium dihydrogen phosphate, 1 mM EDTA (pH 3) and acetonitrile in a 15% ratio and was delivered at a flow rate of 0.7 ml/min. Peaks were detected by electrochemical detection (Coulochem, ESA, Bedford, Mass., USA). The retention times for apomorphine and NPA were 6 and 8 min, respectively. The linearity of the calibration curve was established from 0 to 100 ng/ml of plasma. The detection limit was 0.5 ng/ml.

The determination of the pharmacokinetic parameters using plasma apomorphine concentrations was obtained with a computer program (Siphar Release 4.0).

Non-compartmental Approach

The time to peak plasma concentration (tmax) and the peak plasma concentration (Cmax) were determined by the inspection of data. The area under the concentration-time curve from 0 to the last time (AUC) was determined using the trapezoidal method and the area extrapolated to infinity calculated from the elimination rate constant ($k_{el}$) and the last measured concentration. The bioequivalence factor (F) was calculated by dividing AUC for percutaneous administration by the AUC after subcutaneous route. $K_{el}$ was estimated by a linear regression using the last points of curve after a logarithmic transformation. The apparent volume of distribution ($V_d$), the total clearance (Cl) and the elimination half-life ($T_{1/2}\beta$) were determined from the measured parameters and the administered dose (D) using the following formulas:

$$Vd=(F \times D)/(AUC \times k_{el}) \qquad \text{I}$$

$$Cl=k_{el} \times Vd \qquad \text{II}$$

$$T_{1/2}\beta=\log(2/k_{el}) \qquad \text{III}$$

Compartmental Approach

For subcutaneous administration, individual apomorphine plasma levels were fitted to a sum of three exponentials:

$$C_{(t)}=2362.69e^{-0.039t}+19.25e^{-0.0076t}-2382e^{-0.054t} \qquad \text{IV}$$

in which $C_{(t)}$ is the plasma drug concentration at time t. Pharmacokinetic modeling was performed using the exponential peeling method in order to determine the initial parameters and the nonlinear regression adjustment. The minimization algorithm was based on the Powell method and the objective function was the extended least square method with a weighting of data by 1/y. The final parameters of the fitted function were used to calculate AUC, Vd at steady state (Vdss), mean residence time (MRT) and transfer rate constants ($k_{12}$, $k_{21}$, $k_{13}$).

The Loo-Riegelman method, applicable for a two compartment model, was used on the means of the transfer rate constants determined from the subcutaneous route to evaluate for each individual the percentage apomorphine absorbed for the subcutaneous and the percutaneous routes.

The results were expressed as the mean ± standard error of the mean (SEM). The rank sum test was used to evaluate differences between model-independent pharmacokinetic parameters and the time for absorption after subcutaneous and percutaneous routes. Significance was declared at $p<0.05$.

Results

Figure 5:
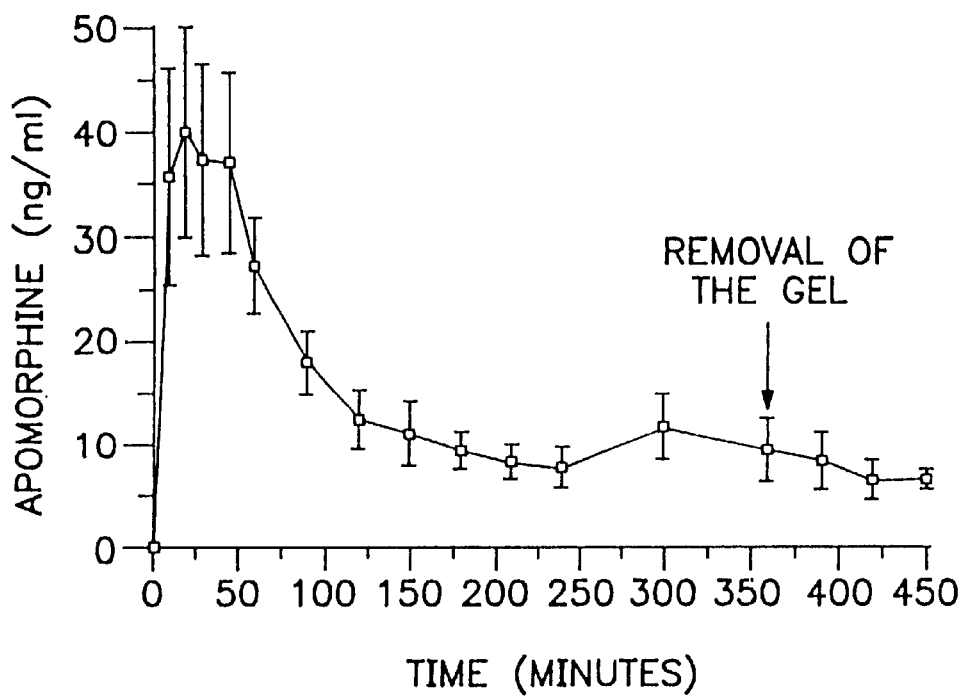
FIG. 5 shows the time course of the plasma concentration of apomorphine after percutaneous administration (0.5 mg/kg) in rabbit (n=8). Filled squares are mean experimental values, error bars are standard error of the mean (SEM), and the smooth curve is a function fitted to the experimental values.
Figure 6:
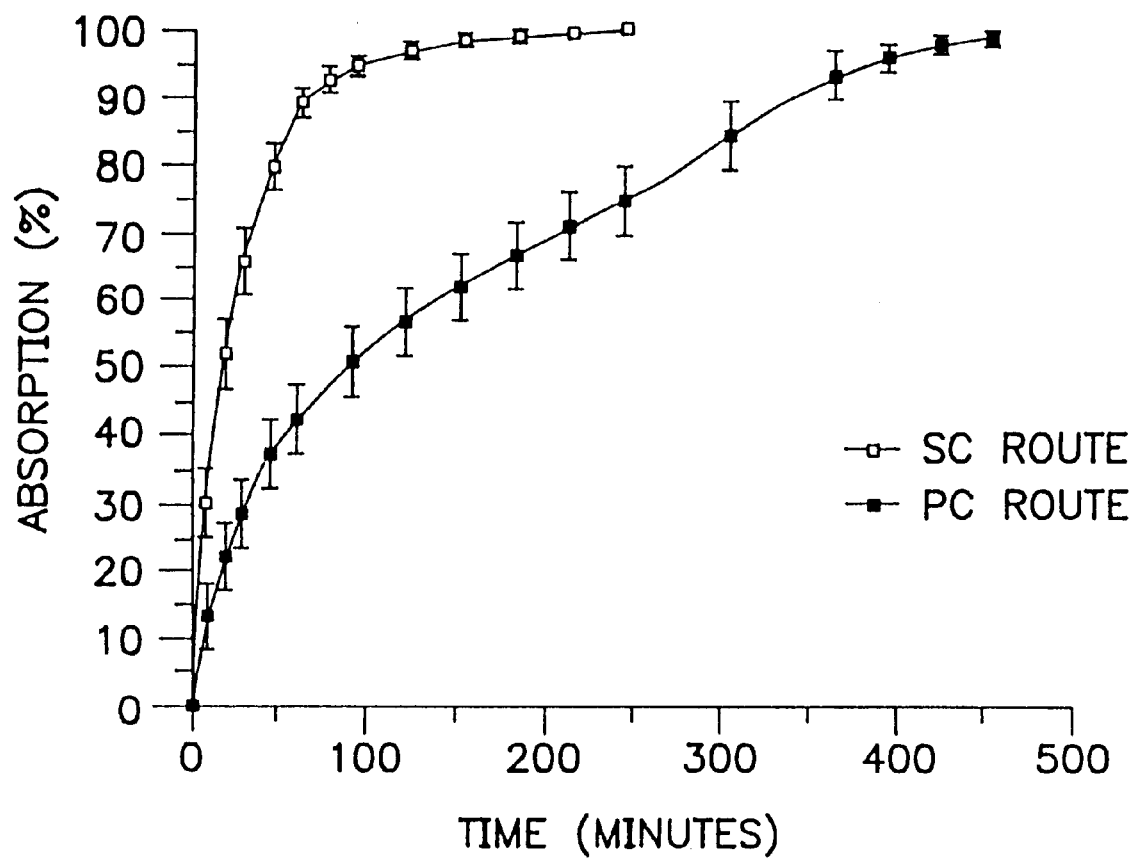
FIG. 6 shows the kinetics of the mean absorption of apomorphine after subcutaneous (n=6) and percutaneous (n=8) administration in rabbit, calculated by the Loo-Riegelman method. Bars indicate SEM.

After subcutaneous administration the plasma levels of apomorphine rapidly rose to a mean Cmax of 331±46 ng/ml and a tmax of 25.8±4.9 minutes. The plasma concentration levels then gradually decreased and were still detectable at 240 minutes (mean: 3.0±1.0 ng/ml), FIG. 5. After apomorphine administration by the percutaneous route, the tmax was similar (29.4±7.8 minutes). After the peak, the plasma levels rapidly decrease until the second hour, but thereafter remained stable at a mean plasma level of 10 ng/ml. In three animals, an increase in the plasma concentration between the fourth and the fifth hour was observed. After removal of the gel, at the sixth hour, the plasma levels decreased (FIG. 6). The mean Cmax was 56±12 ng/ml (Table IV, below).

Other mean model-independent parameters are also given in Table IV for both routes. Cmax and AUC were significantly greater with the subcutaneous route. Cl was not different between the two routes but Vd, $k_{el}$, $T_{1/2}\beta$, MRT were significantly greater with the percutaneous route. The bioequivalence of the percutaneous route was 35% of the subcutaneous administration.

The plasma concentrations of apomorphine time-curves could be described by a two-compartment open model. After subcutaneous administration the time course was fitted by the sum of three exponentials (Formula IV, above). The resulting model-dependent parameters are given in Table V, below. $T_{1/2}\beta$ and Vdss were 34.6±9.8 minutes and 1.1±0.3 l/kg respectively (mean ± standard deviation). After the percutaneous administration, the calculated values obtained with the different compartmental models tested were very different from the experimental values. Thus, it was not possible to calculate the model-dependent pharmacokinetic parameters of apomorphine.

After the subcutaneous route, the absorption, as estimated by the curve of the absorbed percentage of the available amount of the drug, was rapid and practically complete after 150 minutes (time for absorption of 90% of the drug: 68.3±4.7 minutes). After the percutaneous administration, the absorption of apomorphine was rapid during the first 90 minutes, then it slowed and persisted until the $450^{th}$ minute (i.e., even after the removal of the gel at the $360^{th}$ min) (time for absorption of 90% of the drug: 321.3±20.0 minutes) (Table VI, below; FIG. 6).

The pharmacokinetic results obtained after the subcutaneous administration showed a rapid absorption and elimination as an important distribution. These data are in line with those obtained in man after subcutaneous injections [tmax (range): 7–16 min, $T_{1/2}\beta$ (range): 34–70 minutes, Vd (mean): 2 l/kg] and i.v. injection [$T_{1/2}\beta$ (mean): 48 minutes, Vd (mean): 2 l/kg], which illustrate a similitude between the two routes confirmed by the similar bioavailability of the subcutaneous vs the i.v. administration. This point and the usual subcutaneous administration of apomorphine in man have justified our choice of the subcutaneous route to compare the pharmacokinetic parameters obtained after percutaneous administration.

The evaluation of the plasma levels of apomorphine after percutaneous administration in rabbit showed an absorption of the drug in all tested animals. Tmax was rapid and close to the tmax obtained after subcutaneous administration. However, the kinetics of absorption was very different between the two routes. First, the absorption of the available amount of the drug was at 90% at the $68^{th}$ minute for subcutaneous administration and at the $321^{th}$ minute for the percutaneous route. Second, the percentage of absorption increased regularly after the subcutaneous route whereas two phases were observed after the percutaneous administration. The first phase was rapid (1 hour) and might correspond to a transfollicular absorption. The second phase was slower and persisted until the end of the study even after the removal of the gel, suggesting a transdermal absorption or possibly a delayed liberation of the drug from the subcutaneous tissue due to the high lipidic solubility of the drug. The dose-dependent pharmacokinetic parameters (Cmax and AUC) were lower after the percutaneous route. The bioequivalence of the percutaneous route was 35% of the subcutaneous route, suggesting that the absorption of the drug after a percutaneous administration was lower than after the subcutaneous route.

After the tmax, the plasma levels of apomorphine after the percutaneous route decreased and a plateau was observed from the second to the sixth hour between 10 and 15 ng/ml. This stability of the plasma drug concentrations was reflected by the more prolonged MRT observed after percutaneous than after the subcutaneous route, suggesting a balance between the absorption and the elimination of apomorphine, possibly explained by the prolonged transdermal absorption. $K_{el}$ and $T_{1/2}\beta$ were more prolonged after the percutaneous route probably because the terminal elimination constant was modified by the persistence of the entry of apomorphine in the systemic circulation. No local adverse effect was observed after the percutaneous route.

TABLE IV

Model-independent Pharmacokinetic Parameters of Apomorphine (0.5 mg/kg)
Mean ± SEM

| PARAMETER | SUBCUTANEOUS ROUTE (N = 6) | PERCUTANEOUS ROUTE (N = 8) | SIGNIFICANCE |
|---|---|---|---|
| Cmax[1] (ng/ml) | 331 ± 46 | 56 ± 12 | P <0.05 |
| tmax[2] (minutes) | 25.8 ± 4.9 | 29.4 ± 7.8 | |
| AUC[3] (ng · min/ml) | 17828 ± 2281 | 6220 ± 1006 | P <0.01 |
| $1/k_{el}$[4] (min) | 0.021 ± 0.002 | 0.014 ± 0.002 | P <0.05 |
| Vd[5] (l/kg) | 1.45 ± 0.12 | 2.72 ± 0.36 | P <0.05 |
| Cl[6] (l/kg/min) | 0.031 ± 0.005 | 0.037 ± 0.001 | |
| T½β[7] (min) | 34.5 ± 3.5 | 58.1 ± 7.5 | P <0.05 |
| MRT[8] (min) | 50 ± 2 | 168 ± 19 | P <0.01 |

[1] Peak plasma concentration
[2] Time to peak plasma concentration
[3] Area under the concentration vs time curve
[4] $k_{el}$: elimination time constant
[5] Apparent volume of distribution
[6] Total clearance
[7] Elimination half life
[8] Mean residence time of the drug

TABLE V

Model-dependent Pharmacokinetic Parameters (Mean ± SEM) for Apomorphine (0.5 mg/kg) given Subcutaneously in Rabbit (n = 6)

| PARAMETER | MEAN | SEM | CV[1] |
|---|---|---|---|
| A[2] (ng/ml) | 712 | 177 | 61 |
| B[2] (ng/ml) | 298 | 43 | 35 |
| $C_0^2$ (ng/ml) | 1,010 | 139 | 34 |
| $\alpha^3$ (1/min) | 0.044 | 0.008 | 34 |
| $\beta^3$ (1/min) | 0.021 | 0.002 | 25 |
| $k_a^3$ (1/min) | 0.088 | 0.002 | 44 |
| $k_{12}^4$ (1/min) | 0.005 | 0.002 | 105 |
| $k_{21}^4$ (1/min) | 0.027 | 0.006 | 37 |
| $k_{13}^4$ (1/min) | 0.057 | 0.009 | 38 |
| $T_{½}\alpha^5$ (min) | 18.9 | 3.5 | 45 |
| $T_{½}\beta^6$ (min) | 34.7 | 4.5 | 29 |
| $T_{½}k_a$ (min) | 8.8 | 1.1 | 29 |
| Vdss (1/kg) | 1.13 | 0.33 | 29 |
| AUC[7] (ng · minml) | 18,568 | 2,416 | 32 |
| MRT[8] (min) | 52 | 3 | 15 |

[1]COefficient of variation (standard deviation/mean)
[2]Coefficients of the fitted function
[3]Exponents of the fitted function.
[4]Transfer rate constants between the compartments of the model
[5]Absorption half life
[6]Elimination half life
[7]Area under the concentration vs time curve
[8]Mean residence time of the drug

TABLE VI

Mean Time for Absorption of Apomorphine Mean ± SEM

| ABSORBED PERCENTAGE | SUBCUTANEOUS ROUTE (N = 6) (Minutes) | PERCUTANEOUS ROUTE (N = 8) (Minutes) | SIGNIFICANCE |
|---|---|---|---|
| 10% | 4.0 ± 0.7 | 11.4 ± 3.4 | P <0.05 |
| 50% | 19.9 ± 2.9 | 105.7 ± 23.9 | P <0.01 |
| 90% | 68.3 ± 4.7 | 321.3 ± 20.0 | P <0.01 |

EXAMPLE 4

Transdermal Patches Without Enhancers

Transdermal patches (3 cm and 5 cm in diameter) are prepared for the delivery of apomorphine. The patches are composed of a trilaminate of an adhesive matrix sandwiched between an occlusive backing layer and a release liner. The adhesive matrix is prepared from the pressure sensitive silicone adhesive composition BIOPSA® (obtained from Dow Corning Corp., Midland, Mich. 48686) in cyclohexane (50% w/v) together with apomorphine (at concentrations of 0, 0.1, 0.5, 1.0 and 2.0 weight percent. The occlusive backing film is a SCOTCHPAK® 1006 (3M Co., St. Paul, Minn.) polyester film (about 2.8 mil in thickness). The release liner is a polyester film (about 2.9 mil in thickness) of SCOTCHPAK® 1022 (3M Co., St. Paul, Minn.). The final transdermal patches are about 16 mil thick, 3 or 5 cm in diameter and have a surface area of about 7.1 $cm^2$ or 9.6 $cm^2$. In use, the transdermal patch is applied to a patient by removing the release liner and contacting the adhesive unit with the skin of the patient.

EXAMPLE 5

Effect of Apomorphine and Permeation Enhancer Content Upon Properties of Transdermal Patches Patches are prepared as described in EXAMPLE 4. Transdermal patches containing 0, 0.1, 0.5, 1 or 2 weight % apomorphine are evaluated in vitro. The performance of the patches with regard to (1) the removal of the release liner (Release), (2) adhesion to artificial surface, (Adhesion), and (3) tack (Tack) are evaluated. Addition of apomorphine alone or apomorphine with either BHT or HPBCD does not significantly degrade Release, Adhesion and Tack properties.

EXAMPLE 6

Preparation of Apomorphine-containing Transdermal Patches with Enhancers

A solution of BIOPSA® Q7-2920 (50 weight percent in hexane, available from Dow Corning Corp., Midland, Mich. 48686) is filtered through 16-ply Dacron® mesh to remove any particles present from the solution.

Aliquots of the filtered solution (100 gm each) are mixed with sufficient apomorphine to produce individual solutions containing 0, 0.1, 0.5 and 1.0 weight percent, respectively, of apomorphine.

Individual solutions are then mixed with sufficient amounts of a hydroxypropyl-beta-cyclodextrin (HPBCD) with a degree of substitution (D.S.) of 5 to 7 to result in solutions containing 0, 1, 5 and 10 weight percent, respectively, or with BHT solution containing 0, 0.1, 0.5, 1, 5 and 10 weight percent, respectively.

Each solution is mixed for three minutes and then sonicated (50% duty cycle, microtip limit output of continuous cycle) for three minutes. The individual solutions are stored in bottles sealed with Teflon® FEP Film and capped. Each bottle is mechanically rolled during storage to prevent drug settling.

The transdermal patches are prepared as follows. One of the above solutions (50 ml) is poured onto a sheet of SCOTCHPAK® 1022 release liner containing shims (1"× 12"×0.20" thick) placed along the edges (9" apart) and held in place by a tension bar on a coater. The adhesive solution is drawn down (165 inches/min) at a setting of 5.5 on the motor scale. The formulations are air-dried for 24 hours to allow the solvent to evaporate. A sheet of SCOTCHPAK® 1006 polyester film occlusive backing material is transfer-coated onto the dried formulation, smoothed and laminated with a 4.5–5 pound rubber roller.

EXAMPLE 7

Effect of BHT Concentration Upon Patch Properties

Transdermal patches are prepared as described in EXAMPLE 6 with BHT as the permeation enhancer at concentration of 0, 0.1, 0.5, 1, 5 and 10 weight percent. Patches that contain either 0.1 weight percent, 0.5 weight percent or 1.0 weight percent of BHT exhibit the most desirable properties of easy removal of the release liner, adequate tack and good skin adhesion. At BHT levels above 1 weight percent the properties of the patch are substantially reduced and patches tend to stick together.

EXAMPLE 8

Apomorphine Release from Transdermal Patch

An apomorphine transdermal patch formulation was prepared by adding 1 milliliter of a ethanolic solution of 20 mg/ml apomorphine HCl and 2.6 mg/ml glutathione to 2 g of polydimethylsiloxane 200 and mixing until the mixture congealed.

Glutathione acted as an antioxidant to stabilize the apomorphine composition. We have found that glutathione is also an acceptable antioxidant for emulsions comprising apomorphine HCL, glutathione and gels obtained from acrylic acid polymers such as Carbopol 9340. and adjusted to pH 7.6. Glutathione is bio-compatible and non-acidic, thereby minimizing the possibility of dermal irritation following prolonged contact with transdermal compositions.

One milliliter of the above ethanolic apomorphine/glutathione solution was applied to a 47 mm borosilicate filter and set aside to dry under nitrogen until the mixture was absorbed by the filter. This formulation was designated as "Patch A."

A comparison patch, designated "Patch B," was made by applying an aliquot of the above ethanolic apomorphine/glutathione solution to a control patch. The control patches was prepared according to EXAMPLE 4, above, with the modification that the apomorphine was omitted from the adhesive matrix composition when the patch was initially constructed. After 300 µl of the above ethanolic apomorphine/glutathione solution was applied to a control patch, the patch was allowed to dry under nitrogen.

Apomorphine release from the patches was studied using the USP Dissolution Apparatus, Type II. The release medium was deionized water at 32 degrees C., agitated at 30 rpm. The patches were weighted to make them sink in the dissolution vessel. Samples were withdrawn at the times 0, 2, 4, 7, 10, 15, 30, 45, 60, 120, 180 and 360 minutes.

Figure 7:
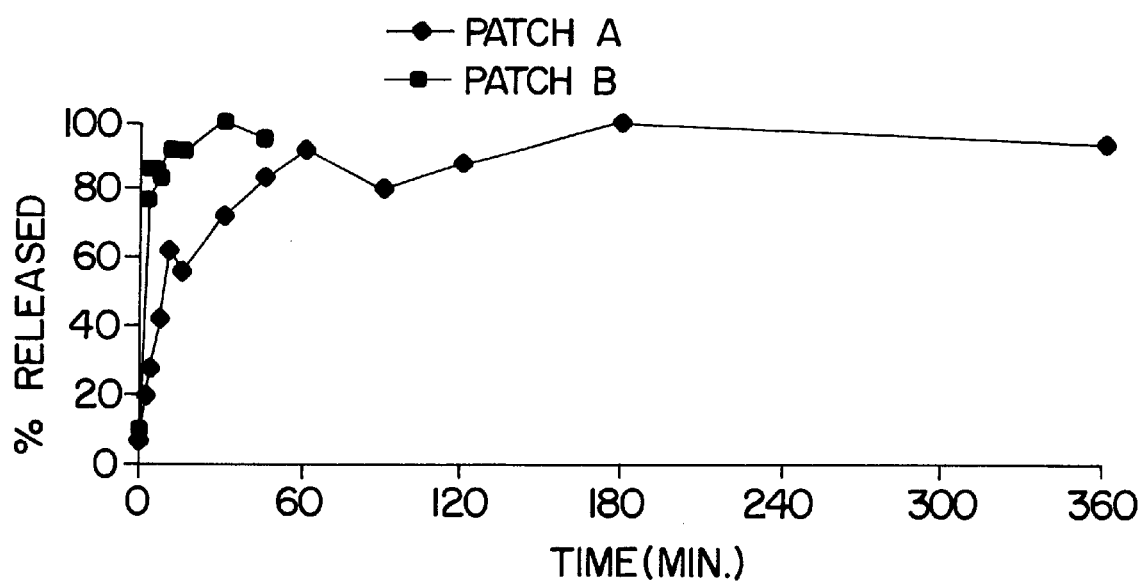
FIG. 7 shows the release over time of apomorphine from two silicone adhesive patch formulations.

Each 1 ml sample was diluted with 1 ml of 0.2N HCl and filtered through a 0.45 µm pore filter. Standards of apomorphine HCl in 0.1N HCl were prepared, and a calibration curve of absorbance at 274 nm (measured by UV spectrophotometer) versus apomorphine concentration was constructed. Apomorphine concentration in the samples was calculated from the measurement of absorbance at 274 nm using the calibration curve. The percent apomorphine released was calculated and plotted against time. The results are shown in FIG. 7.

Patch A released 92% of the apomorphine in the first 60 minutes; the remaining 8% was released during the next 2 hours. Patch B released 100% of the apomorphine in the first 30 minutes. The formulation of Patch A was found to provide a more extended, controlled release of apomorphine compared to Patch B.

The foregoing description and the EXAMPLES are intended as illustrative and are not to be taken as limiting. Still other variations within the spirit and scope of this invention are possible and will readily present themselves to those skilled in the art.

We claim:

1. A dosage form for transdermal delivery of an active form of apomorphine which comprises an adhesive matrix constituted by a medical-grade pressure-sensitive silicone copolymer adhesive, the active form of apomorphine distributed in said matrix in an amount in the range of about 0.1 to about 3 percent by weight of the matrix, and a permeation enhancer for said active form of apomorphine present in said matrix in an amount in the range of about 1 to about 10 percent by weight of the matrix, said permeation enhancer being a carbocyclic compound with pendant hydroxyl groups and selected from the group consisting of butylated hydroxyanisole, butylated hydroxytoluene and hydroxypropyl-beta-cyclodextrin, and mixtures thereof wherein said adhesive matrix containing apomorphine is placed in intimate contact with a patient's skin.

2. The dosage form of claim 1, wherein said adhesive matrix is composed of a plurality of coextensive matrix layers, each layer containing an amount of an active form of apomorphine and permeation enhancer different from that in each matrix layer contiguous thereto.

3. The dosage form of claim 1 further comprising an occlusive backing layer coextensive with said matrix.

4. The dosage form of claim 3, wherein said dosage form is a transdermal patch.

5. The dosage form of claim 4, wherein said permeation enhancer is butylated hydroxyanisole.

6. The dosage form of claim 4 wherein said permeation enhancer is butylated hydroxytoluene.

7. The dosage form of claim 4 wherein said permeation enhancer is a hydroxypropyl-beta-cyclodextrin.

8. The dosage form of claim 7, wherein said hydroxypropyl-beta-cyclodextrin has a degree of substitution of about 5 to about 7.

9. The dosage form of claim 2, wherein each of said coextensive layers contains, independently, a permeation enhancer present in an amount of up to 10 percent by weight of the layer, with the proviso that the total amount of permeation enhancer present in all the layers is in an amount in the range of about 1 to about 10 percent by weight of said adhesive matrix.

10. The dosage form of claim 9, wherein each of said coextensive layers contains, independently, an active form of apomorphine in an amount in the range of about 0.1 to about 10 percent by weight of the layer, with the proviso that the total amount of apomorphine present in all the layers is in an amount in the range of about 0.1 to about 1 percent by weight of said adhesive matrix.

11. The dosage form of claim 10, wherein contiguous independent layers of said adhesive matrix contain different permeation enhancers.

12. The dosage form of claim 11, wherein said dosage form is a transdermal patch comprising an occlusive backing layer coextensive with an adhesive matrix, said adhesive matrix comprising a first layer contiguous with said occlusive backing layer and comprising an active form of apomorphine and a hydroxypropyl-beta-cyclodextrin, and a second layer, contiguous with said first layer, comprising apomorphine and BHT.

13. The dosage form of claim 11, wherein said dosage form is a transdermal patch comprising an occlusive backing layer coextensive with an adhesive matrix, said adhesive matrix comprising a first layer contiguous with said occlusive backing layer and comprising an active form of apomorphine and a hydroxypropyl-beta-cyclodextrin, a second layer, contiguous with said first layer comprising apomorphine and BHT, and a third layer, contiguous with said second layer, comprising BHT.

* * * * *

UNITED STATES PATENT AND TRADEMARK OFFICE
CERTIFICATE OF CORRECTION

PATENT NO. : 5,939,094
DATED : August 17, 1999
INVENTOR(S) : Franck Durif et al.

It is certified that error appears in the above-indentified patent and that said Letters Patent is hereby corrected as shown below:

Title Page, item "[73] Assignee:", "Pharamaceticals" should be -- Pharmaceuticals --, i.e., the Assignee should read as follows:
Pentech Pharmaceuticals, Inc.

Signed and Sealed this
First Day of February, 2000

Attest:

Q. TODD DICKINSON

*Attesting Officer*   *Acting Commissioner of Patents and Trademarks*